United States Patent [19]
von Angerer et al.

[11] Patent Number: 4,992,553
[45] Date of Patent: Feb. 12, 1991

[54] DIAMINE-PLATINUM (II) COMPLEX COMPOUNDS

[75] Inventors: Erwin von Angerer, Grassling; Norbert Knebel, Ingolstadt; Helmut Schönenberger, Pentling; Jürgen Engel, Alzenau, all of Fed. Rep. of Germany

[73] Assignee: Asta Pharma Aktiengesellschaft, Frankfurt am Main, Fed. Rep. of Germany

[21] Appl. No.: 438,984

[22] Filed: Nov. 20, 1989

Related U.S. Application Data

[63] Continuation of Ser. No. 104,135, Oct. 5, 1987, abandoned.

[30] Foreign Application Priority Data

Oct. 3, 1986 [DE] Fed. Rep. of Germany ....... 3633673

[51] Int. Cl.$^5$ .................. A61K 31/555; C07D 401/12; C07D 209/20; C07D 209/14
[52] U.S. Cl. ..................................... 546/12; 548/402; 546/273
[58] Field of Search .......................... 514/186; 548/402

[56] References Cited

U.S. PATENT DOCUMENTS 4,704,464 11/1987 Brunner ............................ 548/402

FOREIGN PATENT DOCUMENTS 2111478 7/1983 United Kingdom .
2128615 11/1984 United Kingdom .
2147578 10/1985 United Kingdom .

OTHER PUBLICATIONS

Bowler, J. A. C. S. 106, 6102 (1984).
T. A. Connors et al. Platinum Coordination Complexes in Cancer Chemotherapy, Berlin, 1974, pp. 132–136.
Sandra J. Meischen et al., Journ. Nat. Cancer Inst. 57, (1976) pp. 841–845.
Sarma et al., Chem–Biol Interactions, 46 (1983) pp. 219–232.
Lalit Kumar et al., Synthesis and Spectroscopic Studies of Potential Anticancer [Platinum(II)(2,2'-Bipyridine)-(Amino acid)]$^{n+}$(n=1 or 2) Complexes; Journal of Inorganic Biochemistry, vol. 23 (1985) pp. 1–11.

Primary Examiner—Mark L. Berch
Attorney, Agent, or Firm—Cushman, Darby & Cushman

[57] ABSTRACT

A compound of the general formula:

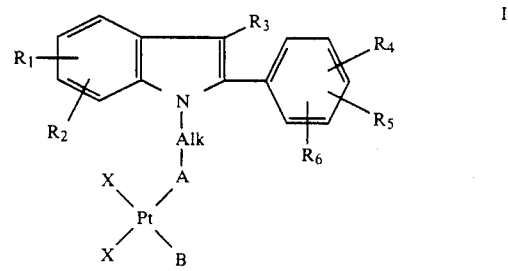

wherein $R_1$ is hydrogen, a hydroxy group or a $C_2$–$C_6$ alkanoyloxy group, $R_2$ is hydrogen or a halogen atom, $R_3$ is hydrogen or a $C_1$–$C_6$ alkyl group, $R_4$ is a hydroxy group or a $C_2$–$C_6$ alkanoyloxy group, $R_5$ is hydrogen or a halogen atom and $R_6$ is hydrogen or a halogen atom, Alk is a $C_2$–$C_{10}$ alkylene chain where 4 neighboring $CH_2$ groups may also be replaced by a 1,4-phenylene ring, A-B is the group HN—$CH_2$—$CH_2$—$NH_2$, $H_2N$—$CH_2$—CH—$CH_2$—$NH_2$ or

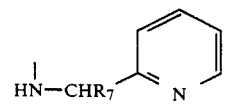

and $R_7$ is a hydrogen atom, a $C_1$–$C_6$ alkyl group or a phenyl radical and X stands for the equivalent of a physiologically acceptable anion. The compound is useful for the treatment of hormone dependent tumors.

3 Claims, No Drawings

DIAMINE-PLATINUM (II) COMPLEX COMPOUNDS

This is a continuation of application Ser. No. 104,135, filed Oct. 5, 1987, now abandoned.

The invention relates to novel diamine-platinum (II) complex compounds with a hydroxylated 2-phenylindole ring which may be used as active substances in medicaments.

BACKGROUND OF THE INVENTION

British patent specification No. 2,111,478 relates to tumor inhibiting indole derivatives of the formula

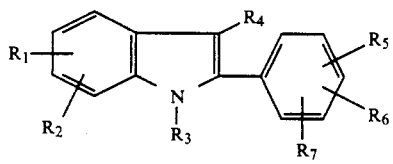

wherein $R_1$ is hydrogen, a hydroxy group or a $C_2$–$C_6$ alkanoyloxy group, $R_2$ is hydrogen, a hydroxy group, a $C_2$–$C_6$ alkanoyloxy group or a halogen atom, $R_3$ is a $C_1$–$C_6$ alkyl group, $R_4$ is hydrogen or a $C_1$–$C_6$ alkyl group, $R_5$ is a hydroxy group or a $C_2$–$C_6$ alkanoyloxy group, $R_6$ is hydrogen or a halogen atom and $R_7$ is hydrogen or a halogen atom.

Furthermore, tumor inhibiting ethylene diamine-platinum (II) complexes are known, wherein a $CH_2$ group of the ethylene diamine is substituted by a benzyl radical, phenylethyl radical, thienylmethyl radical, indolylmethyl radical or imidazolylmethyl radical (German patent specification DE-OS No. 36 05 191) or wherein both $CH_2$ groups of the ethylene diamine contain a phenyl radical or a substituted phenyl radical (German patent specifications DE-OS Nos. 34 05 611; DE-OS 36 04 866).

SUMMARY OF THE INVENTION

The object of the present invention is to provide novel diamine-platinum(II) complex compounds which have a hydroxylated 2-phenylindole ring and which possess a pronounced anti-tumor effect with good tolerability.

The compounds of the invention have the formula:

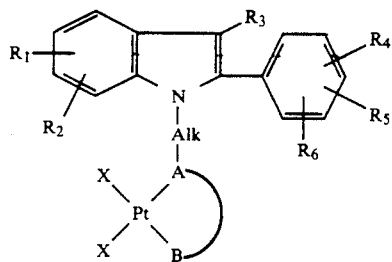

wherein $R_1$ is hydrogen, a hydroxy group or a $C_2$–$C_6$ alkanoyloxy group, $R_2$ is hydrogen or a halogen atom, $R_3$ is hydrogen or a $C_1$–$C_6$ alkyl group, $R_4$ is a hydroxy group or a $C_2$–$C_6$ alkanoyloxy group, $R_5$ is hydrogen or a halogen atom and $R_6$ is hydrogen or a halogen atom, Alk is a $C_2$–$C_{10}$ alkylene chain where 4 neighboring, $CH_2$ groups may also be replaced by a 1,4-phenylene ring,

is the group

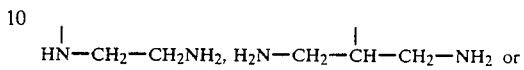

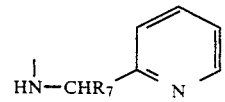

and $R_7$ is a hydrogen atom, a $C_1$–$C_6$ alkyl group or a phenyl radical and X stands for the equivalent of a physiologically acceptable anion.

The present invention also provides a process for the preparation of compounds of the above general formula I which comprises reacting a tetrahalo-platinum (II) acid, a tetrahalo-platinum(II) complex salt, which has two monovalent cations or one bivalent cation, or a platinum(II)-halide with a compound of the formula:

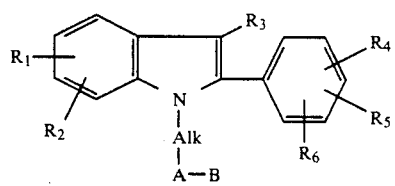

or a salt of the compound II, where the radicals $R_1$, $R_2$, $R_3$, $R_4$, $R_5$, and $R_6$ and the groups Alk and A-B have the meanings given above. Optionally, the radical X may be exchanged for other physiologically acceptable anions.

The effect of the compounds the present invention is particularly evident in the following animal and cell culture models:

Transplanted hormone dependent MXT-mammary carcinoma of BDF-1 mouse. Estrogen dependent dimethylbenzanthracene induced mammary carcinoma of SD rat. Human hormone dependent MCF-7 breast cancer cells.

The platinum complex compounds of the present invention provide a surprising advance because they possess very high affinity for the estrogen receptor and have a selective effect on estrogen receptor-containing tumors such as mammary carcinoma. This represents the first successful attempt to link a molecule having an affinity for an estrogen receptor with a cytostatically acting diamine platinum group in such a way that the affinity for the receptor and the cytostatic effect ar retained.

The platinum complexes of the invention have, for example, high binding affinity for the estrogen receptor of calves' uteri. The relative binding affinities are of the order of 1–15% of the affinity of estradiol. Despite the strong binding to the estrogen receptor, the complexes do not, however, have an estrogenic effect on the uterus of the mouse. In certain cases a pronounced antiestrogenic effect has been demonstrated (compounds of Examples 2 and 5). A pronounced tumor inhibiting effect was found in transplanted hormone dependent MXT-mammary carcinoma of the mouse. Thus, for example, the inhibitory effect of the compound of Example 1 was 89% after 6 weeks, treatment at a dosage of 20 mg/kg. The inhibitory effect of the compound of Example 2 under the same conditions is 77%.

The compounds of the present invention display a good tumor inhibiting effect for example in transplantable hormone dependent MXT-mammary carcinoma of the BDF-1 mouse or rat. For example, in this experimental model, at a dosage of 20 mg/kg body weight in a mouse, the tumor weight was very much smaller as compared to the controls (for example by 89%).

The lowest effective dosage in the last-mentioned animal experiment is for example 10 mg/kg subcutaneously.

As a general active dosage range (animal experiment as above) one may for example use: 1–50 mg/kg subcutaneously, in particular 5–30 mg.

The direction of the effect of the compounds of the invention is comparable with the effect of the know medically active substance estramustine phosphate. However, the compounds of the invention, unlike this compound, have a high affinity for the estrogen receptor.

Indications for which the compounds of the invention may be considered include: hormone dependent mammary carcinoma, carcinoma of the prostate, endometrial carcinoma and melanoma.

Contraindications: pregnancy.

The following are examples of groups which may be used as the substituent R, the alkylene bridge Alk, the group A-B and the acid anions X.

The $C_1$–$C_6$ alkyl groups and $C_2$–$C_6$ alkanoyloxy groups present in the individual radicals $R_1$ and $R_7$ as well as the alkylene bridge Alk may be straight or branched chain groups. The alkyl groups preferably contain 1, 2, 3 or 4 carbon atoms, the alkanoyloxy groups preferably 2–4 carbon atoms (preferably the acetoxy group). The $R_3$ radical is preferably methyl, the radical $R_7$ preferably hydrogen, methyl, ethyl or phenyl. The $R_1$ radical is preferably in the 5- or 6-position of the indole ring. The $R_4$ radical is preferably in the 4-position of the phenyl ring, the radicals $R_5$ and $R_6$ are preferably in the 2- and/or 6-positions. The alkylene bridge Alk consists for example of 4 to 8 $CH_2$ groups, preferably 5, 6 or 7 $CH_2$ groups. In the event that four neighboring $CH_2$ groups of Alk are replaced by a 1,4-phenylene ring, these may be four neighboring $CH_2$ groups which are not bound to a nitrogen atom, or the phenylene ring may also be directly linked to a nitrogen atom or with both nitrogen atoms. In the latter case, the Alk bridge represents the 1,4-phenylene ring. The $R_2$ radical is located, for example, in the 4-position of the indole ring.

Further examples for Alk groups which contain a phenylene ring are:

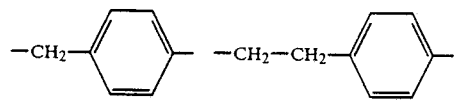

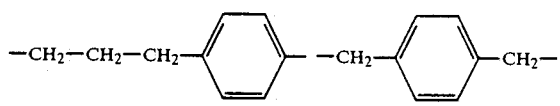

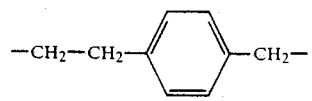

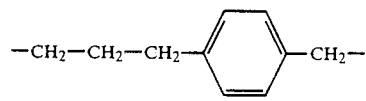

The halogen substituents may be, in particular, chlorine, bromine and/or fluorine.

The radicals X represent the known and conventional physiologically acceptable and pharmaceutically useable anions of mono- or polyvalent acids. In particular, the anions of the following acids may be used: HBr, HCl, HI, HF, $HNO_3$, $H_2SO_4$ ($SO_4^{--}$); $H_3PO_4$, ($HPO_4^{--}$); $H_2CO_3$ ($CO_3^{--}$); camphor sulfonic acid, aliphatic or aromatic sulfonic acids, for example $C_1$–$C_6$ alkyl sulfonic acids (for example methane sulfonic acid, ethane, propane or hexane sulfonic acid, in particular o- or p-toluene sulfonic acid); aliphatic $C_1$–$C_4$ monocarboxylic acids, which may be mono-, di- or trisubstituted by halogen atoms (in particular Cl, F) (for example formic acid, acetic acid, propionic acid, chloroacetic acid, dichloroacetic acid, trifluoroacetic acid, trichloroacetic acid); aliphatic $C_2$–$C_{11}$ dicarboxylic acids which may contain a double bond (for example oxalic acid, malonic acid 2-amino malonic acid, malonic acid substituted in the 2-position by a benzyl group or by one or two $C_1$–$C_4$ alkyl groups, maleic acid, fumaric acid, succinic acid); aliphatic monohydroxy and dihydroxy-mono-carboxylic acids with 2 to 6, in particular 2 to 3 carbon atoms, whereby these are preferably α-monohydroxy-carboxylic acids such as lactic acid, glyceric acid or glycolic acid; aliphatic monohydroxy and dihydroxy, di- and tricarboxylic acids with 3 to 8 carbon atoms, in particular 3 to 6 carbon atoms, such as malic acid, tartaric acid, malonic acid, which may be substituted at the central carbon atom by a hydroxy group and optionally by a $C_1$–$C_4$ alkyl group, isocitric acid or citric acid; phthalic acid, which may optionally be substituted by a carboxy group (in particular in the 4-position); gluconic acid, glucuronic acid; 1,1-cyclobutanedicarboxylic acid; organophosphoric acids such as aldose and ketose phosphoric acids (for example the corresponding mono and diphosphoric acids) for example aldose-6-phosphoric acids such as D- or L-glucose-6-phosphoric acid, α-D-glucose-1-phosphoric acid, D-fructose-6-phosphoric acid, α-D-galactose-6-phosphoric acid, D-ribose-5-phosphoric acid, D-fructose-1,6-diphosphoric acids; glycerine phosphoric acids (where the phosphoric acid radical is bound to one of the terminal glycerine oxygen atoms or to the central glycerine oxygen atom) such as α-D,L-glycerine phosphoric acid, B-glycerine phosphoric acid; N-phosphono-acetyl-asparaginic acid.

It is also possible to use, as acids which form the anions X, amino acids or amino acid derivatives having a basic amino group neutralized by an acid group. These may for example be amino acids having the following structure:

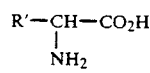

wherein R' is hydrogen, a phenyl radical, an indolyl-(3)-methyl radical, imidazolyl-(4)-methyl radical, a $C_1$–$C_{10}$ alkyl group or a $C_1$–$C_{10}$ alkyl group which is substituted by a hydroxy group, a carboxy group, a $C_1$–$C_6$ alkoxy group, a mercapto group, a $C_1$–$C_6$ alkylthio group, a phenyl group, a hydroxyphenyl group, a $C_2$–$C_6$ alkanoylamino group or a $C_1$–$C_6$ alkoxy carbonyl group.

The basic amino group in the 2- position may be neutralized by a conventional amino acid protecting group (acylated) for example by a $C_2$–$C_6$ alkanol radical or the butyloxycarbonyl radical.

Should R' in the above formula be an alkyl group, this is preferably a $C_1$–$C_6$ alkyl group which contains for example in the 2, 3, 4, 5 or 6 position (counting begins at the linkage point of the alkyl radical with the rest of the molecule) a $C_2$–$C_6$ alkanoylamino group, an imidazolyl-(4)-methyl radical or an indolyl-(3)-methyl radical. Individual examples for such amino acids are: leucine (preferably D- and L-form), valine (preferably D- and L-form), phenylalanine (preferably D- and L-form), phenylglycine (preferably D- and L-form), alanine (preferably D- and L-form), isoleucine (preferably D- and L-form), asparagin (preferably D- and L-form), lysine (preferably D- and L-form), tryptophan (preferably D- and L-form), tyrosine (preferably D- and L-form), ornithine (preferably D- and L-form).

In this case the basic amino groups are blocked by a conventional acylamino protecting group, in particular by the acetyl group or the butyloxycarbonyl group.

Formula I also includes all possible enantiomers and diastereomers. Should the compounds be racemates, these may be separated in known manner, for example using an optically active acid, into the optically acitve isomers. It is, however, also possible to use enantiomeric or optionally also diastereomeric starting materials from the outset, so that the end product thus obtained is a corresponding pure optically active or diastereomeric compound. Additional forms may result through various enantiomeric or diasteromeric forms of the radicals X.

The compounds of formula I may optionally contain water and may then also be present as diaquo complexes, where 2 molecules of water ar complexed onto the platinum; the anion X or the anions X also neutralize the double positive charge of the $Pt^{++}$ cation in these cases.

In the case of the platinum atom, the compounds of the invention of Formula I are always the cis-compounds.

The starting amine II is for example used as a racemate, as an exclusively right or left-rotating form or in another diastereomeric form. This configuration is maintained during the production of the platinum complex.

The process for the production of the compounds I of the invention is carried out in a solvent or suspension agent at temperatures between 10° and 80° C., preferably 20° to 50° C., in particular 35° to 45° C. The solvents that may be used are, for example: water, $C_1$–$C_6$ alkanols (methanol, ethanol, tert-butanol), tetrahydrofuran, dioxane, lower dialkylsulfoxides (for example dimethylsulfoxide), $C_1$–$C_4$ mono- or dialkylamides of $C_1$–$C_4$ alkane carboxylic acids (for example dimethylformamide), ethylene-glycol dimethylether, diethyleneglycol dimethylether as well as mixtures of these solvents, in particular mixtures with water.

The two reaction components (platinum compound and compound II) are preferably used in equimolar amounts. The pH of the reaction solution should be between 5.5 and 8, preferably pH 7. The adjustment of the pH should in particular be effected by addition of alkali, preferably aqueous sodium or potassium hydroxide solution or, for example, also using sodium carbonate or through the addition of acids, preferably aqueous hydrochloric acid.

Tetrahalo-platinum(II) compounds (acid as well as complex salts) that may be used include the corresponding tetrachloro, tetrabromo and tetraiodo compounds. Should platinum(II)-halides be used as starting materials, the same halogen atoms may be used.

Monovalent cations that may be used are: alkali ions, in particular sodium and potassium; it is, however, also possible to use lithium, rubidium, caesium as well as $NH_4^+$, $NR_4^+$, $PR_4^+$ or $AsR_4^+$, in which R is a $C_1$–$C_6$ alkyl radical or a phenyl radical. Bivalent cations may be: alkaline earth metal ions, in particular $Mg^{2+}$ and $Ca^{2+}$, but also $ZN^{2+}$. The platinum-(II)-halides may for example be $PtCl_2$, $PtBr_2$ and $PtI_2$.

Compound II is either used in the form of the diamine or in the form of an acid addition salt: for example as monohydrochloride or dihydrochloride, mono- or dihydrobromide, mono- or dihydroiodide or as a salt with another conventional acid, such as sulphuric acid, nitric acid or perchloric acid. It is in particular also possible to use acids, the anions of which form the radicals X. Furthermore, the diamine may be used in the form of the acetate or diacetate, in which case potassium chloride (for example 2 moles per 1 mole of compound II) may optionally be added to the reaction components before mixing. The diamine II may also be used in the form of the carbonate.

The exchange of the ligands X for other ligands may for example be effected by means of silver halide precipitation. In this case for example a dihalo-diamine-platinum(II) compound of formula I, where X is halogen (chlorine, bromine or iodine) is caused to react in a solvent or suspension agent at temperatures between 0° and 90° C., preferably 10° to 50° C., in particular 30° to 40° C., especially 40° with the silver salts of another acid, which corresponds to the group X. One may, however, also use silver nitrate as the silver salt (for example aqueous silver nitrate solution), whereby one obtains an ionic diaquo complex of formula I, where every X represents a water molecule which is then di-positively charged and is neutralized by two $NO_3^-$ anions.

The weakly bound ligand water may easily be displaced from this complex by anions having a higher affinity therefor (for example $Cl^-$, $Br^-$) in the form of NaCl, KCl, NaBr, KBr, $malonate^{2-}$, chloracetate-, $oxalate^{2-}$, 1,1-cyclobutanedicarboxylic acid $anion^{2-}$ as well as the other mentioned acid radicals X, used in the form of the acids or their salts, in particular their alkali salts.

The same compounds may also be obtained by reaction of equimolar amounts of HX and nitrate-free platinum complex (the latter also with the use of anion exchangers in the hydroxide form, for example Dowex 1-8X).

An exchange of the leaving group (for example $SO_4^{2-}$ or oxalate $anion^{2-}$) is also possible in the case of the sulphato- or oxalato-diamine-platinum(II) compounds by reaction with alkaline earth metal salts which contain the desired X-ligands (for example glyceric acid), provided the complex so formed is water soluble and thus permits the separation of the poorly soluble alkaline earth metal sulphate or oxalate.

X-ligands suitable for this process are preferably the anions of hydroxycarboxylic acids, sulfonic acids, haloacetic acids and nitric acid.

The solvents or suspension agents set out for the process for the preparation of compounds I may also be used for the exchange reaction (particularly suitable are water and dimethylformamide as well as methanol, ethanol, tert-butanol). The exchange reaction is for example conducted in a pH range between 3 and 7.

The production of unknown starting substances of formula II may for example be carried out as set out in the individual examples, or in a manner analogous thereto.

The production of such starting compounds may for example be carried out as follows:

The appropriate indole compound with the meanings given above for $R_1$ to $R_6$ (hydroxy groups are advantageously etherified, for example methylated) is converted into the derivative in the conventional way using NaH or an equivalent alkali compound/alkali metal where the hydrogen of the indole nitrogen is replaced by an alkali metal. This indole derivative is then caused to react in a solvent or suspension agent at temperatures between $-70°$ and $+80°$ C. with a Hal-Alk-Hal compound (Hal being for example bromine); the compound thus obtained, which contains the group Alk-Hal at the indole nitrogen, is now caused to react in a solvent or suspension agent (for example lower alcohols, lower dialkyl ethers or also amines HA-B) at temperatures between 10° and 150° C. with an amine HA-B. Finally, any ether groups (methyl groups) which may be present are split off in the conventional maner (for example using $BBr_3$ in a halogenated hydrocarbon at 0° to 50° C.) Instead of the reaction with the amine HA-B, the halogen atom of the Alk-Hal group may also be replaced by the $NH_2$ group (for example by conventional reaction with potassium phthalimide in an organic dialkylamide at temperatures between 50° and 180° C.). The introduction of the A-B group is then effected by means of reaction with a corresponding aldehyde or ketone (the structural part $H_2N\text{-}CH_2$ or $H_2N\text{-}CHR_7$ of HA-B is then the group $CH=O$ or $CR_7=O$). This reaction is for example conducted in a conventional manner in an inert solvent between 70° and 50° C. Subsequently the double bond of the so-obtained Schiff's base is reduced and any ether groups present are split off. Should the group

the meaning

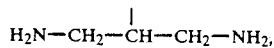

the production of the corresponding starting materials is effected for example as follows: conventional reaction of malonic acid dinitrile in the presence of NaH with the corresponding indole derivative, where the indole nitrogen contains the Alk-Hal group, in an inert medium at temperatures between 0° and 80° C., reduction of the two nitrile groups to amino groups (for example by means of complex alkali hydrides of aluminium or boron at temperatures between 0° and 150° C.) and optional subsequent splitting off of ether groups.

In starting substances of Formula II or of the materials from which they are made, any hydroxy groups present may be acylated by $C_2\text{-}C_6$ alkanoyl groups. This acylation may for example be conducted by means of $C_2\text{-}C_6$ alkanoyl halides or the anhydrides of the saturated aliphatic $C_2\text{-}C_6$ mono-carboxylic acids at temperatures between 10° and 80° C., in particular 20° to 30° C., in the presence of conventional acid binding agents. Acid binding agents which may in particular be used include aliphatic tertiary amines, such as for example diisopropylethylamine. Inert solvents or suspension agents which may for example be used for the acylation include: lower aliphatic halohydrocarbons (chloroform), aprotic solvents such as amides, $C_1\text{-}C_4$ alkylamides and $C_1\text{-}C_4$ dialkylamides of aliphatic $C_1\text{-}C_4$ carboxylic acids (dimethylformamide, dimethylacetamide), N-methyl-pyrrolidone, dimethylsulfoxide or mixtures of these agents.

This acylation may, however, for example also be conducted in a two-phase system for example water/chloroform, whereby the acylated platinum(II) complex obtained with the aid of an anion exchanger separates off as being insoluble and the mixture of acid chloride and tertiary amine (diisopropylethylamine) is in the chloroform phase. Acid halides which may advantageously be used are the corresponding chloride, bromide and optionally iodide. The anhydrides may be benzoic acid anhydride as well as the anhydrides of $C_1\text{-}C_6$ carboxylic acids, for example symmetrical acid anhydrides such as acetic anhydride, propionic acid anhydride, butyric acid anhydride.

It may be appropriate under certain circumstances to provide any free amino groups present with clevable protecting groups prior to such an acylation. Protecting groups that may be used are those conventionally used in peptide synthesis (for example tert-butyloxycarbonyl group, 2-nitrophenylsulfenyl group). Following the acylation these protecting groups are split off in known manner.

The compounds of the invention are suitable for the preparation of pharmaceutical compositions. The pharmaceutical compositions or medicaments may contain one or several of the compounds of the invention or also mixtures thereof with other pharmaceutically active substances. The medications may for example be given interally, parenterally (for example intravenously, intramuscularly, subcutaneously) or orally.

Pharmaceutical formulations of these compounds contain, in general, between 10 and 500 mg, preferably 20 to 200 mg and especially 20 to 50 mg of the active component(s) of the invention.

These pharmaceutical compositions may be in the form of tablets, capsules, pills, dragees, suppositories, ointments, gels, creams, powder, dusting powder, aerosols or in liquid form, using conventional pharmaceutical carriers and auxilliary substances.

Liquid forms of application may be solutions in oils, for example sesame or olive oil, alcohol or aqueous media, as well as suspensions and emulsions in these liquids. Preferred forms of administration include tablets containing between 20 and 50 mg of active ingredient and solutions containing between 0.2 and 2 percent of active ingredient.

In addition it is possible to prepare dry ampoules which contain as active substance the compound I of the invention, whereby the contents of such dry ampoules are dissolved before use for example in physiological salt solution or in mixtures of physiological salt solution and for example liquid polyethyleneglycols.

The individual dose of the active components of the compounds of the invention may be
(a) in the case of oral administration of the medication, between 10 and 500, preferably 20-200 mg.
(b) in the case of parenteral forms of medication (for example intravenous, intramuscular) between 10 and 200 mg, preferably between 20 and 100 mg.

For example, the medication may be administered 3 times daily in a dose of 1 to 3 tablets containing from 10 to 50 mg of active substance each time. The daily dose should be a minimum of 50 mg and a maximum of 500 mg.

In the case of intravenous injection, 1 to 3 injections may be given using, in each case, an ampoule containing 5 to 20 ml of medicine which contains 25 to 100 mg of the active ingredient.

The acute toxicity of the compounds of the invention in the mouse (expressed as LD 50, mg/kg; method according to Miller and Tainter: Proc. Soc. Exper. Biol. a. Med. 57 (1944) 261) is, in the case of subcutaneous administration, above 20 mg/kg.

DETAILED DESCRIPTION OF THE EMBODIMENTS

The invention is illustrated by the following examples.

General procedure for the preparation of the platinum complexes 1.01 mmol of the corresponding diaminoindole of Formula II are dissolved in 10 ml of dimethylformamide, stirred slowly and heated to 40° C. 1.01 mmol of $K_2PtCl_4$ are then dissolved in a mixture of 10 ml of dimethylformamide-$H_2O$ (5:2 volume/volume) and slowly added dropwise using a pipette.

The mixture is stirred for 24 hours with exclusion of light and then mixed with 2 ml of dimethylsulfoxide until a pale yellowish coloration appears. Following a further 2 hours' stirring, the solvent mixture is distilled off under an oil pump vacuum. The brown oily residue is mixed with water until pale yellow crystals precipitate out. The product is suction filtered and washed several times with ethanol. Purification is carried out by taking up in dimethyl-formamide and precipitating with ethanol/water (1:1 volume/volume), suction filtering and drying for several days. Under certain circumstances it may be necessary to repeat the precipitation several times in order to obtain the complex compound in pure form.

The compounds produced are listed in Table 1. The indole part has the following structure for the compounds of Table 1:

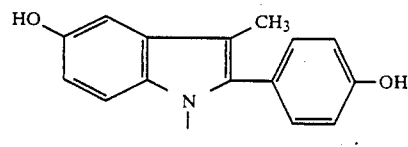

TABLE 1

| Example No. | Group $\begin{smallmatrix} X \\ \\ X \end{smallmatrix} \!\! \diagdown \!\! \begin{smallmatrix} Alk \\ | \\ A \\ \\ Pt \\ \\ B \end{smallmatrix}$ | Decomposition point °C. | Structure Alk-A—B of starting compound II |
|---|---|---|---|
| 1. | —(CH$_2$)$_6$—NH     NH$_2$ \ / Pt / \ Cl   Cl | as from 130 | —(CH$_2$)$_6$—NH—CH$_2$—CH$_2$—NH$_2$ |
| 2. | —(CH$_2$)$_4$—NH     NH$_2$ \ / Pt / \ Cl   Cl | as from 161 | —(CH$_2$)$_4$—NH—CH$_2$—CH$_2$—NH$_2$ |
| 3. | —(CH$_2$)$_5$—NH     NH \ / Pt / \ Cl   Cl | as from 140 | —(CH$_2$)$_5$—NH—CH$_2$—CH$_2$—NH$_2$ |
| 4. | —(CH$_2$)$_6$— NH$_2$   Cl \ / Pt / \ NH$_2$   Cl | 169 | —(CH$_2$)$_6$—CH(CH$_2$NH$_2$)$_2$ |

TABLE 1-continued

| Example No. | Group $\begin{array}{c} X \\ X \end{array} Pt \begin{array}{c} A-Alk \\ B \end{array}$ | Decomposition point °C. | Structure Alk-A—B of starting compound II |
|---|---|---|---|
| 5. | —(CH₂)₄—CH(NH₂)(NH₂)—Pt(Cl)(Cl) | as from 180 | —(CH₂)₄CH(CH₂NH₂)₂ |
| 6. | —(CH₂)₅—CH(NH₂)(NH₂)—Pt(Cl)(Cl) | as from 155 | —(CH₂)₅CH(CH₂NH₂)₂ |
| 7. | —CH₂—C₆H₄—CH₂—NH—(CH₂)—NH₂—Pt(Cl)(Cl) | 195–200 | —CH₂—C₆H₄—CH₂—NH—CH₂—CH₂—NH₂ |
| 8. | —(CH₂)₆—NH—CH₂-(2-pyridyl)—Pt(Cl)(Cl) | | —(CH₂)₆—NH—CH₂-(2-pyridyl) |
| 9. | —(CH₂)₅—NH—CH₂-(2-pyridyl)—Pt(Cl)(Cl) | | —(CH₂)₅—NH—CH₂-(2-pyridyl) |
| 10. | —(CH₂)₄—NH—CH₂-(2-pyridyl)—Pt(Cl)(Cl) | | —(CH₂)₄—NH—CH₂-(2-pyridyl) |

Preparation of the starting compound for Example 1

1.
1-(6-bromohexyl)-5-methoxy-2-(4-methoxyphenyl)-3-methyl-indole 12.5 mmol (300 mg) of NaH are added to 40 ml of absolute dimethylformamide and cooled to 0° C. With vigorous stirring, 7.5 mmol of 5-methoxy-2-(4-methoxyphenyl)-3-methyl-indole dissolved in 25 ml of absolute dimethylformamide are slowly added dropwise and stirred for 30 minutes at 0° C. This suspension is added dropwise with stirring and ice-cooling to a solution of 11.0 mmol of 1,6-dibromohexane in 25 ml of absolute dimethylformamide and stirred for 30 minutes at 0° C. Excess NaH is destroyed with water and stirring continues for a further 2.5 hours at room temperature. The mixture is shaken with dichloromethane, dried over MgSO₄ and the solvent removed. The brown oily crude product is chromatographed on silica gel with dichloromethane and recrystallized from ethanol. Yield 84%. M.P. 60° C.

2.
1-[6-(2-amino-ethylamino)-hexyl]-5-methoxy-2-(4-methoxyphenyl)-3-methyl-indole 6.0 mmol of ethylene diamine are dissolved in 40 ml of anhydrous methanol in a nitrogen atmosphere. 4.0 mmol of the previously prepared 1-(6-bromohexyl)-indole compound in 80 ml of absolute methanol are then added dropwise at room temperature. The mixture is heated for 12 hours under reflux. Following cooling the mixture is extracted with $CH_2Cl_2$ and $H_2O$. Following drying over $Na_2SO_4$ the solvent is drawn off, the remaining colorless oil is subsequently purified by distillation in a high vacuum.

3.
1-(2-amino-ethylamino)-6-[5-hydroxy-2-(4-hydroxyphenyl)-3-methyl-indole-1-yl]-hexane 4.0 mmol of the dimethoxyindole derivative as obtained above are dissolved in 100 ml of anhydrous dichloromethane under a nitrogen atmosphere with dry ice/acetone cooling. The mixture is stirred for 10 minutes and 10.0 mmol of $BBr^3$ (dissolved in 15 ml of anhydrous dichlormethane) are then added dropwise. Stirring continues overnight and the reaction mixture is allowed to come to room temperature. It is subsequently heated for 2 hours under reflux. Methanol is then added dropwise to the product under ice cooling and a stream of nitrogen until the vigorous reaction has subsided. Following removal of the solvent the remaining oil is mixed with saturated $NaHCO_3$ solution and the resulting precipitate is suctioned filtered. The crude product is heated under reflux in a Soxhleth apparatus for 3–5 hours with 200 ml of triethylamine and filtered hot. After the solvent has been distilled off the residue is supended in $H_2O$ and suctioned filtered (decomposition point: 112°–114° C.). In the case of the starting substances for the other examples, this splitting of the ether group is conducted in analogous manner.

In an analogous manner one ma obtain the starting materials for Examples 2, 3 and 7.

Preparation of the starting compound for Example 4:

1.
6-[5-methoxy-2-(4-methoxyphenyl)-3-methyl-indole-1-yl-]-hexyl-malonic acid dinitrile 5.0 mmol of NaH are suspended in 30 ml of absolute tetrahydrofuran in a nitrogen atmosphere and with ice cooling. 5.0 mmol of malonic acid dinitrile are then dissolved in 30 ml of absolute tetrahydrofuran and slowly added dropwise. 1-(6-bromohexyl)-5-methoxy-2-(4-methoxyphenyl)-3-methyl indole that has previously been dissolved in 30 ml of absolute tetrahydrofurane is now added slowly dropwise at room temperature. Stirring continues for a further 15 minutes at room temperature and the product is subsequently mixed with 20 ml of water. The product is extracted with ether and water, dried over $MgSO_4$ and the solvent is distilled off. The brown oily crude product is chromatographed on silica gel with dichloromethane and dichloromethane/ethyl acetate (10;1 volume/volume). Recrystallization is effected from ether. Yield: 48%, M.P. 93°–95° C.

2.
1-amino-2-aminomethyl-6-[5-methoxy-2-(4-methoxyphenyl)-3-methyl-indole-1-yl]-octane 9.5 mmol of $LiAlH_4$ are suspended in 40 ml of absolute tetrahydrofuran under ice cooling. To this 2.5 mmol of the dinitrile dissolved in 30 ml of absolute tetrahydrofuran are slowly added dropwise under vigorous stirring. The reaction mixture is refluxed for 30 hours at 100° C. After cooling, the product is mixed with 60 ml of ether with ice cooling and mixed with water to destroy excess $LiAlH_4$.

The precipitate is suctioned off, the filtrate dried over KOH and $K_2CO_3$ and the solvent removed on a rotary evaporator. The product so obtained is a colorles to weakly yellow colored, viscous oil. The reaction may be monitored by means of IR spectroscopy of the disappearance of the CN band at 2265 $cm^{-1}$ and the appearance of the $NH_2$ band at 3380 $cm^{-1}$ Yield: 80%.

By splitting off of the two methoxy groups (in analogous manner to that described in Example 1) one obtains the starting compound II for Example 4: 1-amino-2-aminomethyl-6-[5-hydroxy-2-(4-hydroxyphenyl)-3-methyl-indole-1-yl]-octane.

The starting materials for Examples 5 and 6 may be prepared in an analogous manner.

Preparation of the starting compound for Example 8:

1-(6-amino-hexyl)-5-methoxy-2-(4-methoxyphenyl)-3-methyl-indole 8.0 mmol of 1-(6-bromohexyl)-5-methoxy-2-(4-methoxy-phenyl)-3-methyl indole and 8.8 mmol of phthalamidepotassium are heated in 100 ml of anhydrous dimethylformamide for 2 hours under reflux. Following cooling the product is shaken with dichloromethane and $H_2O$. The product is then dried over $Na_2SO_4$ and the solvent distilled off. The residue is chromatographed on silica gel with dichloromethane. To liberate the amine the so-obtained colorless crystals are taken up in 50 ml of ethanol (99%) and mixed with hydrazine hydrate in 20 ml of ethanol. The mixture is now heated for 2 hours under reflux; after cooling, it is acidified with 40 ml of 2 N HCl solution and suctioned off from the precipitate. After distilling off the solvent the mixture is made alkaline with 40 ml of 2 N NaOH and extracted three times with ethyl acetate. The mixture is then dried over $Na_2SO_4$ and chromatographed on silica gel with dichloromethane/ethyl acetate (10:1, volume/volume). A viscous colorless to yellowish oil is obtained.

2.
5-methoxy-2-(4-methoxyphenyl)-3-methyl-1-6-(2-pyridyl-methylamino)-hexyl]-indole Formation of Schiff's base 10.0 mmol of 2-pyridinealdehyde are mixed with 11.0 mmol of the 6-aminohexylindole obtained according to 1 in 60 ml of dry benzene and heated in a Soxhleth apparatus with anhydrous $CaSO_4$ for 24 hours under reflux. Following removal of the solvent the condensation product which takes the form of a viscous oil is taken up in diethyl ether and dried over $Na_2SO_4$. The pure Schiff's base is obtained in the form of a yellow viscous oil by means of short-path distillation in a high vacuum.

Reduction of the Schiff's base to amine:

A solution of 10.0 mmol of the Schiff's base in 40 ml of anhydrous methanol cooled to −10° C. is added to 12.0 mmol of $NaBH_4$. It is allowed to warm up to room temperature over a period of 2 hours and then stirred for 12 hours at 50° C. After removal of the methanol 20 ml of $H_2O$ are added, the mixture is shaken three times with ether and dried over $Na_2SO_4$. After short-path distillation in a high vacuum, the amine is obtained as a yellow viscous oil.

Splitting off of the methoxy groups is effected in the same way as for Example 1.

The starting materials of Formula II for the other examples in Table 1 may be obtained in analogous manner.

Table 2 relates to compounds with a different indole group. The Alk-diamine-dichloroplatinum group has the same structure in Examples 15–17 as in Example 1:

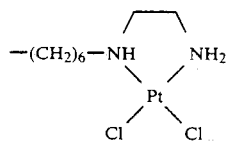

In the case of Examples 18 and 19 the alk-diamine-chloroplatinum group has the same structure as in Example 2:

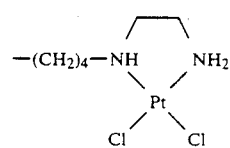

TABLE II

| Example No. | Group | Decomposition point °C. | Structure Alk-A—B of starting compound II |
|---|---|---|---|
| 11. | —(CH₂)₇—NH, CH₂-pyridyl, Pt, Cl, Cl | as from 128 | —(CH₂)₇—NH—CH₂-(2-pyridyl) |
| 12. | —(CH₂)₆—NH, CH(CH₃)-pyridyl, Pt, Cl, Cl | as from 142 | —(CH₂)₆—NH—CH(CH₃)-(2-pyridyl) |
| 13. | —(CH₂)₆—NH, CH(C₂H₅)-pyridyl, Pt, Cl, Cl | as from 133 | —(CH₂)₆—NH—CH(C₂H₅)-(2-pyridyl) |
| 14. | —CH₂-C₆H₄-CH₂-CH(CH₂-NH₂)(CH₂-NH₂)-Pt-Cl₂ | as from 198 | —CH₂-C₆H₄-CH₂CH(CH₂NH₂)(CH₂NH₂) |

| Example No. | Indole portion | Decomposition point °C. | Structure Alk-A—B of starting compound II |
|---|---|---|---|
| 15. | 5-HO-indole-2-(4-hydroxyphenyl) | as from 155 | as Example 1 |

TABLE II-continued

| | | | |
|---|---|---|---|
| 16. | 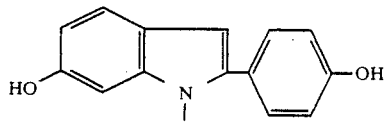 | as from 160 | as Example 1 |
| 17. | 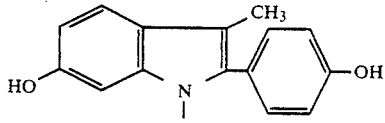 | as from 128 | as Example 1 |
| 18. | 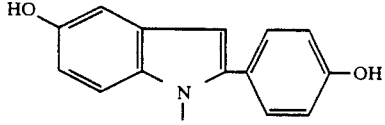 | as from 140 | as Example 2 |
| 19. | 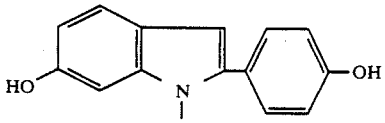 | as from 104 | as Example 2 |

Examples of pharmaceutical formulations

Example of tablets 200 g of the compound of Example 2, 500 g of lactose, 360 g of micronized cellulose, 130 g of corn starch and 10 g of magnesium stearate are passed through a sieve of mesh size 1.0 mm and homogenized in an appropriate mixer. This mass is pressed into 120 mg tablets in the conventional manner. Each tablet contains 20 mg of active ingredient.

Example of coated tablets

In order to produce coated tablets, tablets corresponding to Example 1 are coated in known manner using a spray device with a film soluble in the stomach or small intestine, said film being composed of a suitable polymer film former such as for example esters of acrylates or methacrylates and suitable auxiliary agents such as wetting agents, plasticizers, dyes, lubricants, etc. The tablets may also be processed into dragees in conventional manner.

Example of dry substance for injections 2 kg of the compound of Example 1 are crystallized out under sterile conditions, dried and ground under sterile conditions in a suitable mill (for example Condux mill). The particle size of the substance ready for filling should be between 50 and 250 $\mu$m. The sterile, ground active ingredient is filled using an appropriate worm batching unit at 100 mg portions in 40 ml injection vials. For intravenous use the dry substance is dissolved in 10 ml of an appropriate solvent (for example polyethylene glycol 400/0.9% aqueous salt solution 1:1). For every injection vial an appropriate ampoule with solvent is prepared. Each 10 ml injection vial contains 100 mg of active substance. One ampoule contains 10 ml of solvent.

What is claimed is:

1. A compound of the formula:

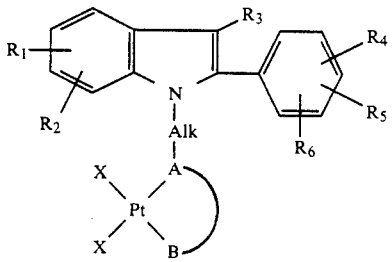

wherein $R_1$ is hydrogen, a hydroxy group or a $C_2$–$C_6$ alkanoyloxy group, $R_2$ is hydrogen or a halogen atom, $R_3$ is hydrogen or a $C_1$–$C_6$ alkyl group, $R_4$ is a hydroxy group or a $C_2$–$C_6$ alkanoyloxy group, $R_5$ is hydrogen or a halogen atom and $R_6$ is hydrogen or a halogen atom, Alk is a $C_2$–$C_{10}$ alkylene chain where 4 neighboring $CH_2$ groups may also be replaced by a 1,4-phenylene ring,

is the group

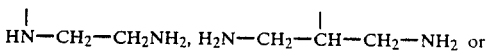

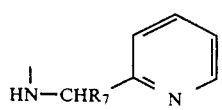

and $R_7$ is a hydrogen atom, a $C_1$–$C_6$ alkyl group or a phenyl radical and X stands for the equivalent of a physiologically acceptable anion.

2. A compound having the formula:

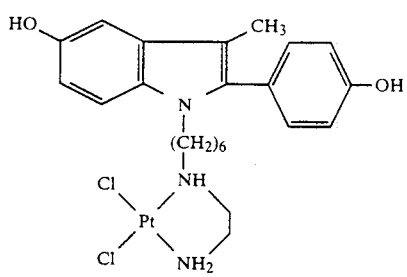
3. A compound having the formula:
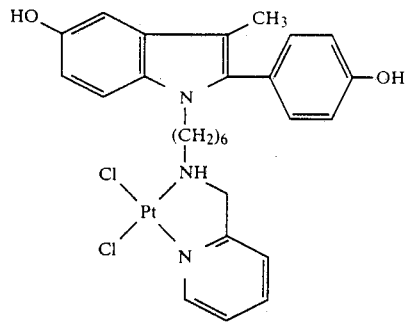
* * * * *